United States Patent [19]

Grosse

[11] 4,242,511
[45] Dec. 30, 1980

[54] PRODUCTION OF AMINE SALTS OF ACID O,S-DIALKYLTHIOPHOSPHORIC ACID

[75] Inventor: Jürgen Grosse, Hürth, Fed. Rep. of Germany

[73] Assignee: Hoechst Aktiengesellschaft, Fed. Rep. of Germany

[21] Appl. No.: 72,084

[22] Filed: Sep. 4, 1979

[30] Foreign Application Priority Data

Sep. 7, 1978 [DE] Fed. Rep. of Germany ....... 2838933

[51] Int. Cl.³ .................. C07D 295/00; C07F 9/165; C07F 9/65
[52] U.S. Cl. ................................. 544/110; 260/987; 546/22
[58] Field of Search ................ 260/925, 987; 544/110; 546/22

[56] References Cited

U.S. PATENT DOCUMENTS 3,839,505  10/1974  Oswald et al. ........................ 260/925

Primary Examiner—Anton H. Sutto
Attorney, Agent, or Firm—Connolly and Hutz

[57] ABSTRACT

The invention relates to an improved process for making amine salts of acid O,S-dialkylthiophosphoric acid esters of the general formula (I)

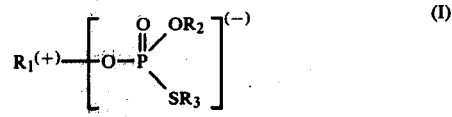

in which $R_1$ stands for the ammonium ion of primary or secondary aliphatic, cycloaliphatic or aromatic amines or of a heterocyclic nitrogen base and $R_2$ and $R_3$ each stand for an alkyl group by subjecting an O,O,S-trialkyl-thiophosphate to partial dealkylation and forming the salt of the dealkylated product by treatment with an amine corresponding to the ammonium ion $R_1$. In the improved process an O,O,S-trialkylthiophosphate of the general formula (II)

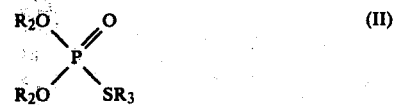

in which $R_2$ and $R_3$ have the meanings given above, is mixed with at least stoechiometric proportions of water and an amine corresponding to the ammonium ion $R_1$, the resulting mixture is reacted, with agitation, over a period of about 3 to 8 hours at a temperature within the range 0° to 120° C., and the amine salt of the general formula (I) is separated from the reaction mixture.

7 Claims, No Drawings

PRODUCTION OF AMINE SALTS OF ACID O,S-DIALKYLTHIOPHOSPHORIC ACID

The present invention relates to a process for making amine salts of acid O,S-dialkylthiophosphoric acid esters from O,O,S-trialkylthiophosphates.

It has already been described (cf. J. Michalski, Roczniki Chem. 33, 247 (1959); J. Chem. Soc. 1962, 5056; and E. V. Jensen, J. Amer. Chem. Soc. 85, 1623 (1962)) that the reaction of sodium dialkylphosphite with a dialkyl or diarylsulfide permits sodium O,S-dialkylthiophosphates to be produced in 40–70% yields in accordance with the following equation:

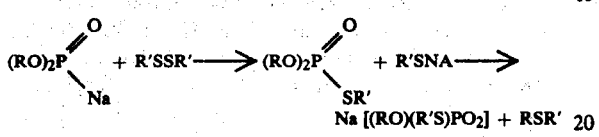

Acidification of the sodium-O,S-dialkylthiophosphate, extraction of the acid ester and reaction of the latter with cyclohexylamine give the corresponding amine salt of the following formula:

Another process for making amine salts of the O-ethyl-S-phenyl-thiophosphoric ester has been described by J. Lecoq and A. R. Todd in J. Chem. Soc. 1954, 2381, wherein O,O-diethyl-S-phenyl-thiophosphate is reacted with lithium chloride to give a compound of the following formula:

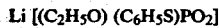

and the lithium salt is acidified with $H_2SO_4$ for conversion to the acid thiophosphoric acid ester, the amine salt being obtained by reacting the latter with cyclohexylamine.

A further process has been described by N. N. Melnikow in Zh. Obshch 33, 2456, (1963), wherein O,O,O-trimethyl-thiophosphate is reacted with triethylamine at 100° C. and over a period of 25 hours to give a compound of the formula:

which is obtained in a yield of 35% of the theoretical.

A. Zwierzak (cf. Synthesis 1975, page 270) has described that the saponification of O,S-dialkyl-O-tertiobutyl-thiophosphoric acid esters with trifluoroacetic acid and reaction of the saponified ester with dicyclohexylamine give compounds of the following formula:

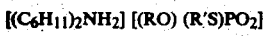

in 82–95% yields, based on the theoretical. Only the O-tertio-butyl ester can, however, successfully be saponified in the process just described.

The prior processes described above are, however, not fully satisfactory in respect of the following points. Long reaction periods are necessary to produce the final products, which are incidentally obtained in unsatisfactory yields or together with by-products which have to be destroyed in costly manner for reasons of environmental protection, or difficultly accessible feed materials are used which do not add to commercial attractiveness.

In view of the fact that O,S-dialkylthiophosphoric acid esters have gained commercial interest as starting materials for making plant protecting agents, the art has been in need of a commercially attractive process for making them, which avoids the adverse effects described hereinabove.

The present invention now provides a process for making amine salts of acid O,S-dialkylthiophosphoric acid esters from readily accessible starting materials which are easy to convert to the desirable final product.

The present invention relates more particularly to a process for making amine salts of acid O,S-dialkylthiophosphoric acid esters of the general formula (I)

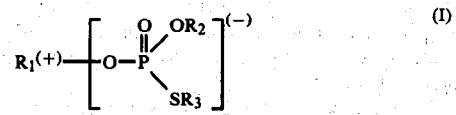

in which $R_1$ stands for the $C_1$–$C_{18}$ ammonium ion of a substituted or unsubstituted primary or secondary aliphatic, cycloaliphatic or aromatic amine or of a heterocyclic nitrogen base, and $R_2$ and $R_3$ each stand for an alkyl group having 1 to 4 carbon atoms, by subjecting an O,O,S-trialkyl-thiophosphate to partial dealkylation and forming the salt of the dealkylated product by treatment with an amine corresponding to the ammonium ion $R_1$, which comprises: mixing an O,O,S-trialkylthiophosphate of the general formula (II)

in which $R_2$ and $R_3$ have the meanings given above, with at least stoechiometric proportions of water and an amine corresponding to the ammonium ion $R_1$, reacting the resulting mixture, with agitation over a period of about 3 to 8 hours at a temperature within the range about 0° to 120° C., and separating the amine salt of the general formula (I) from the reaction mixture.

The amines which are suitable for use in the process of this invention comprise, for example: methylamine, dimethylamine, ethylamine, diethylamine, propylamine, dipropylamine, butylamine, dibutylamine, hydroxyethylamine, dihydroxyethylamine, n-hexylamine, di-n-hexylamine, cyclohexylamine, dicyclohexylamine or methyl-hydroxyethylamine and also piperidine or morpholine, amines having 1 to 6 carbon atoms being preferably used. As to the compounds of general formula (II), it is preferable to use those in which the alkyl group $R_2$ is an ethyl group and $R_3$ stands for a propyl group.

In carrying out the process of the present invention, it is advantageous to mix the O,O,S-trialkylphosphate with the amine and water in a molar ratio of 1:2:1–12, to heat the resulting mixture to 40°–70° C. over a period of 4 to 7 hours and then to separate the amine salt from the reaction mixture. Sometimes, it may be advantageous to use an inert dissolving agent promoting the dissolution of the reactant in water, the useful dissolving agents being selected from ethanol, acetonitrile, dioxane or acetone, for example.

In those cases in which the reaction mixture is an aqueous solution, it is preferable for it to be worked up by first washing it with an inert organic solvent, such as toluene or hexane, then separating the aqueous phase and evaporating the water therefrom, the residue constituting the desired final product. In those cases in which the reaction mixture is a two-phase mixture comprised of an aqueous phase and an organic phase containing the final product, the invention provides for the organic phase to be separated and to be freed distillatively from components more readily volatile than the desired final product, which in this event is obtained as the base product.

The process of the present invention compares very favorably with the prior art methods primarily in the use of readily accessible starting materials which need relatively short reaction periods as compared with those which are normal in the prior art methods. In addition to this, the reaction is carried out under mild conditions and the salts are obtained in yields and with a purity which would not have been expected for this kind of products.

Also, the partial dealkylation in accordance with this invention of the compounds of general formula (II) would not have been expected to simultaneously entail salt formation. A series of tests was made on the dealkylation of compounds of general formula (II) with the use of aqueous alkali metal hydroxide solutions. In this case, it was found that two different reactions, which are illustrated by the two following formulae, were involved in the dealkylation which naturally gave two alkali metal salts in the molar ratio of about 2:1

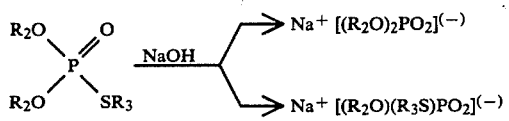

the compound of the following formula

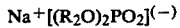

being obtained in a preponderant quantitative proportion.

As compared with this, the process of this invention has been found exclusively to yield the amine salt of the thiophosphoric acid ester which clearly is an unexpected result.

The following Examples illustrate the invention which is, however, not limited thereto.

EXAMPLE 1

212 g (1 mol) of O,O-diethyl-S-n-propylthiophosphate and 225 g of a 40 weight% aqueous dimethylamine solution (corresponding to 2 mols of amine) were heated to 60° C. over a period of 4 hours, with agitation. Next, the reaction solution was allowed to cool down to room temperature, and extracted twice, each time with 200 ml of toluene. The toluene phase was separated and the aqueous phase was concentrated under vacuum to constant weight. 197 g of a slightly yellowish oil was obtained. This corresponded to a yield of 86% of the theoretical. The oil had a refractive index of $n_D^{24}=1.4688$. Elementary analysis and the $^1$H and $^{31}$P-NMR-data evidenced that the product was dimethylammonium-O-ethyl-S-n-propylthiophosphate.

EXAMPLE 2

21.2 g (0.1 mol) of O,O-diethyl-S-n-propylthiophosphate and 15.5 g of a 40 weight% aqueous methylamine solution (corresponding to 0.2 mol of methylamine) were reacted and the reaction mixture was worked up in the manner described in Example 1. 13 g of a yellow oil which had a refractive index of $n_D=1.4680$ was obtained. The $^1$H and $^{31}$P-NMR-data evidenced that the product was methylammonium-O-ethyl-S-n-propylthiophosphate. The yield was 45% of the theoretical.

EXAMPLE 3

The procedure was as in Example 1, but 21.2 g (0.1 mol) of O,O-diethyl-S-n-propylthiophosphate was reacted with 18 g of a 50 weight% aqueous ethylamine solution (corresponding to 0.2 mol of ethylamine). 11 g of a slightly yellowish oil which had a refractive index of $n_D^{23}=1.4681$ was obtained. The $^1$H and $^{31}$P-NMR-data evidenced that the product was ethylammonium-O-ethyl-S-n-propylthiophosphate. The yield was 35% of the theoretical.

EXAMPLE 4

The procedure was as in Example 1, but 22.1 g of O,O-diethyl-S-n-propylthiophosphate was reacted with 36.6 g of a 40 weight% aqueous diethylamine solution. Thiophosphate and amine were used in a molar ratio of 1:2. 13.5 g of a slightly yellowish oil which had a refractive index of $n_D^{23}=1.4643$ was obtained. The $^1$H and $^{31}$P-NMR-data evidenced that the product was diethylammonium-O-ethyl-S-propylthiophosphate. The yield was 50% of the theoretical.

EXAMPLE 5

The procedure was as in Example 1, but a mixture of 21.2 g (0.1 mol) of O,O-diethyl-S-n-propylthiophosphate, 9 g (0.106 mol) of piperidine and 13.5 g (0.75 mol) of water was reacted. 12 g of a light yellow oil which had a refractive index of $n_D^{27}=1.4848$ and corresponded to piperidinium-O-ethyl-S-n-propylthiophosphate was obtained. The yield was 50% of the theoretical. The experiment just described was repeated, but 84.8 g (0.4 mol) of O,O-diethyl-S-n-propylthiophosphate, 68 g (0.8 mol) of piperidine and 102 g of water were used. 79 g of piperidinium-O-ethyl-S-n-propylthiophosphate was obtained in a yield of 70% of the theoretical.

EXAMPLE 6

The procedure was as in Example 1, but 32 g of O,O-diethyl-S-n-propylthiophosphate was reacted with 22 g of n-butylamine in the molar ratio of 1:2 in 35 g of water. 24 g of a yellow oil of which the composition indicated that it was n-butylammonium-O-ethyl-S-n-propylthiophosphate was obtained. The amine salt which had a refractive index of $n_D^{24}=1.4632$ was obtained in a yield of 66% of the theoretical.

EXAMPLE 7

The procedure was as in Example 1, but 84.8 g (0.4 mol) of O,O-diethyl-S-n-propylthiophosphate, 49 g (0.8 mol) of 2-hydroxyethylamine and 102 g (5.66 mols) of water were reacted. 100 g of a slightly yellowish oil which had a refractive index of $n_D^{23}=1.4712$ was obtained. It was identified as being di-n-butylammonium-O-ethyl-S-n-propylthiophosphate. The yield was 62.4% of the theoretical.

EXAMPLE 8

The procedure was as in Example 1, but 63 g of O,O-diethyl-S-n-propylthiophosphate was reacted with 63 g of bis-(2-hydroxyethyl)amine in the molar ratio of 1:2 in 100 g of water. 58 g of a yellow oil which had a refractive index of $n_D^{25} = 1.4813$ was obtained. It was identified as being bis-(2-hydroxyethyl)-ammonium-O-ethyl-S-n-propylthiophosphate. The yield was 50% of the theoretical.

EXAMPLE 9

The procedure was as in Example 1, but 63.6 g of O,O-diethyl-S-n-propylthiophosphate was reacted with 45 g of methyl-(2-hydroxyethyl)amine in the molar ratio of 1:2 in 68 g of water. 52 g of a yellow oil which had a refractive index of $n_D^{23} = 1.48$ was obtained. It was identified as being methyl-(2-hydroxyethyl)ammonium-O-ethyl-S-n-propylthiophosphate. The yield was 70% of the theoretical.

EXAMPLE 10

103 g (5.7 mols) of water, 103 g (0.56 mol) of di-n-hexylamine, 59 g of O,O-diethyl-S-n-propylthiophosphate and 50 g of ethanol as a dissolving agent were heated, with agitation, for 4 hours to 60° C., for 2 hours to 80° C. and for 1 hour to 89° C. During the entire reaction period, the reaction was found to consist of two phases. The upper organic phase was separated from the aqueous phase and volatile constituents were distilled off under vacuum. 85 g of a brown product was obtained as residue. It solidified gradually to give yellow crystals which had a melting point of 44° C. The product was identified as being di-n-hexylammonium-O-ethyl-S-n-propylthiophosphate. The yield was 83% of the theoretical.

EXAMPLE 11

77.4 g (4.3 mols) of water, 77.4 g (0.6 mol) of di-n-butylamine and 63.6 g (0.3 mol) of O,O-diethyl-S-n-propylthiophosphate were heated to 60° C. The batch was found to form two phases which were admixed with 50 ml of ethanol as a dissolving agent. Next, the mixture was heated, with agitation, for 4 hours to 60° C., for 1 hour to 80° C. and for 2 hours to 88° C. After the reaction was complete, the upper organic phase was separated, volatile constituents therein were distilled off under vacuum and the residue was cooled. 47.5 g of di-n-butylammonium-O-ethyl-S-n-propylthiophosphate which had a melting point of 35° C. was obtained. The yield was 51% of the theoretical.

I claim:

1. In the process for making amine salts of acid O,S-dialkylthiophosphoric acid esters of the general formula (I)

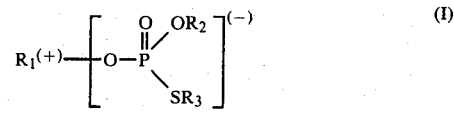

in which $R_1$ stands for the $C_1$-$C_{18}$ ammonium ion of a substituted or unsubstituted primary or secondary aliphatic, cycloaliphatic or aromatic amine or of a heterocyclic nitrogen base, and $R_2$ and $R_3$ each stand for an alkyl group having 1 to 4 carbon atoms, by subjecting an O,O,S-trialkyl-thiophosphate to partial dealkylation and forming the salt of the dealkylated product by treatment with an amine corresponding to the ammonium ion $R_1$, the improvement which comprises: mixing an O,O,S-trialkylthiophosphate of the general formula (II)

in which $R_2$ and $R_3$ have the meanings given above, with water and an amine corresponding to the ammonium ion $R_1$, employing 2 Mols of amine and 1 to 12 Mols of water per mol of phosphate, reacting the resulting mixture, with agitation, over a period of about 3 to 8 hours at a temperature within the range about 0° to 120° C., and separat-ing the amine salt of the general formula (I) from the reaction mixture.

2. The process as claimed in claim 1, wherein $R_1$ stands for the ammonium ion of a primary or secondary amine having 1 to 6 carbon atoms.

3. The process as claimed in claim 1, wherein the amine corresponding to the ammonium ion $R_1$ is methylamine, dimethylamine, ethylamine, diethylamine, propylamine, dipropylamine, butylamine, dibutylamine, hydroxyethylamine, dihydroxyethylamine, n-hexylamine, di-n-hexylamine, cyclohexylamine, dicyclohexylamine or methylhydroxyethylamine or piperidine or morpholine.

4. The process as claimed in claim 1, wherein $R_2$ stands for an ethyl group and $R_3$ stands for a propyl group.

5. The process as claimed in claim 1, wherein the reaction mixture is maintained over a period of 4 to 7 hours at a temperature within the range 40° and 100° C.

6. The process as claimed in claim 1, wherein the reaction mixture is used in admixture with an inert dissolving agent for water and for organic reactants immiscible with water.

7. The process as claimed in claim 6, wherein ethanol, acetonitrile, dioxane or acetone is used as the dissolving agent.

* * * * *